(12) United States Patent
Bornzin et al.

(10) Patent No.: US 6,175,766 B1
(45) Date of Patent: Jan. 16, 2001

(54) CARDIAC PACEMAKER AUTOTHRESHOLD ARRANGEMENT AND METHOD WITH RELIABLE CAPTURE

(75) Inventors: Gene A. Bornzin, Simi Valley; Kerry A. Bradley, Woodland Hills, both of CA (US)

(73) Assignee: Pacesetter, Inc., Sylmar, CA (US)

( * ) Notice: Under 35 U.S.C. 154(b), the term of this patent shall be extended for 0 days.

(21) Appl. No.: 09/282,030

(22) Filed: Mar. 30, 1999

(51) Int. Cl.$^7$ ....................................................... A61N 1/37
(52) U.S. Cl. ............................................................. 607/28
(58) Field of Search .................................. 607/11, 27, 28

(56) References Cited

U.S. PATENT DOCUMENTS

| | | | |
|---|---|---|---|
| 4,543,956 | 10/1985 | Herscovici | 128/419 PG |
| 4,674,509 | 6/1987 | DeCote, Jr. | 128/419 PT |
| 4,708,142 | 11/1987 | DeCote, Jr. | 128/419 PT |
| 4,729,376 | 3/1988 | DeCote, Jr. | 128/419 PT |
| 5,320,643 | 6/1994 | Roline et al. | 607/28 |
| 5,476,487 | 12/1995 | Sholder | 607/28 |
| 5,549,652 | 8/1996 | McClure et al. | 607/28 |
| 5,713,933 | 2/1998 | Condie et al. | 607/28 |
| 5,718,720 | 2/1998 | Prutchi et al. | 607/28 |

Primary Examiner—William E. Kamm

(57) ABSTRACT

There is disclosed a system for determining a pacing energy stimulation threshold of a heart chamber for use in a cardiac pacemaker for applying to the chamber of the heart pacing electrical pulses of sufficient energy so as to exceed a pacing energy stimulation threshold. The system includes a pulse generator which repeatedly applies pacing electrical pulse pairs to the chamber. Each electrical pulse pair includes a first pulse and a second pulse. The first pulse precedes the second pulse and is of lesser energy than the second pulse. The first and second pulses evoke a first and second response respectively of the chamber. A subtractor subtracts the second response from the first response for each pulse pair to provide a series of capture values. The stimulation threshold is selected when the capture values change sign. Also disclosed is a method carried out by the disclosed system.

22 Claims, 3 Drawing Sheets

CARDIAC PACEMAKER AUTOTHRESHOLD ARRANGEMENT AND METHOD WITH RELIABLE CAPTURE

FIELD OF THE INVENTION

The present invention is generally directed to a cardiac pacemaker having a system for automatically determining the pacing energy stimulation threshold of a chamber of a heart and more particularly to such a system and method which assures reliable pacing capture of the chamber as the pacing energy stimulation threshold is determined.

BACKGROUND OF THE INVENTION

Cardiac pacemakers are well known in the art. Such devices apply electrical pulses to one or more chambers of the heart. The energies of such applied electrical pulses are selected to be above the pacing energy stimulation threshold of the respective heart chamber to cause the heart muscle of that chamber to depolarize or contract. Depolarization of the heart muscle of the respective chamber in turn causes the respective chamber to contract. In this manner, the required pumping action of the heart is sustained.

If an applied pulse has an energy below the pacing energy stimulation threshold of the respective chamber, the pacing pulse will be ineffective in causing the heart muscle of the respective chamber to depolarize or contract. As a result, there will be failure in sustaining the pumping action of the heart. It is therefore necessary to utilize applied pacing pulse energies which are assured of being above the pacing energy stimulation threshold.

However, it is also desirable to employ pacing energies which are not exorbitantly above the stimulation threshold. The reason for this is that cardiac pacemakers are usually implanted beneath the skin of a patient and hence are battery powered. Using energies that are too much above the stimulation threshold would result in early depletion of the battery and hence premature cardiac pacemaker replacement.

It is therefore desirable to ascertain the pacing energy stimulation threshold of a heart chamber to be paced. A pacing energy may then be selected which is above the threshold to assure reliable pacing but no so high as to unduly deplete the battery.

As is well known in the art, the stimulation threshold of a heart chamber can, for various reasons, change over time. Hence it is further desirable to have the cardiac pacemaker periodically and automatically determine the pacing energy threshold. In this way, the variations or changes in stimulation threshold can be accommodated to both assure reliable pacing and extended battery life.

When a pacing pulse is effective in causing depolarization or contraction of the heart muscle, it is referred to as "capture" of the heart. Conversely, when a pacing pulse is ineffective in causing depolarization or contraction of the heart muscle, it is referred to as "lack of capture" of the heart.

An electrogram (EGM), as is also well known in the art, is the electrical activity of a heart muscle. The electrical manifestation of lack of capture in a heart muscle is typically a negative deflection in the electrogram baseline. This is referred to as polarization (POL). The electrical manifestation of capture in a heart muscle is typically an exaggerated biphasic deflection in the EGM. This is generally referred to as the evoked response plus polarization (ER+POL).

When a cardiac pacemaker performs a pacing energy stimulation threshold search or test, it is essential that there not be lack of capture because the patient still requires cardiac rhythm management. Generally, these searches are performed by applying a succession of test pacing pulses at a basic rate. The energy of each successive pacing pulse is reduced by a known amount and capture is verified following each pulse. If a test pulse fails to capture, a backup or safety pulse is applied to sustain heart activity. The energy of the test pulse to last capture is then used as a basis for determining the energy threshold. In these methods, capture may be verified by detecting T-waves, mechanical heart contraction, changes in cardiac blood volume impedance, or another signature of a contracting chamber.

Other methods are also known for providing automatic pacing energy stimulation threshold determinations which provide successive pairs of pacing pulses. Each pair of pulses includes a primary pulse and a secondary pulse. The secondary pulse is used to determine an estimate of the polarization and to provide safety pacing. In these techniques, the pulses in the delivered pair have the same amplitude and pulse width so as to provide the same pacing energy. The pulses of each pair are timed such that, if one pulse captures, the other pulse will provide a measure of polarization. The polarization waveform is subtracted from the evoked response plus polarization waveform to determine if capture occurred. Unfortunately, if the capture threshold is below the energy of the two identical pulses of a pulse pair, no provision is made for providing pacing until the next pulse pair. In essence, the primary and secondary pulses are unsuccessful in capturing the heart chamber and as a result, the heart drops a beat. In determining the stimulation threshold of the ventricle, this occurrence is unacceptable.

SUMMARY OF THE INVENTION

The invention therefore provides, in a cardiac pacemaker arranged for applying to a chamber of a heart pacing electrical pulses of sufficient energy so as to exceed a stimulation threshold of the chamber, a system for determining the pacing energy stimulation threshold while providing reliable capture of the chamber. The system includes a pulse generator for repeatedly applying pacing electrical pulse pairs to the chamber. Each electrical pulse pair includes a first pulse and a second pulse, wherein the first pulse precedes the second pulse, and wherein the first pulse is of lesser energy than the second pulse. The first and second pulses evoke a first response and a second response respectively of the chamber. The system further includes means for comparing the first response to the second response to provide capture values, and threshold selecting means responsive to the capture values for selecting a minimum necessary pacing energy to effect capture of the chamber.

The invention further provides in a cardiac pacemaker arranged for applying to a chamber of a heart pacing electrical pulses of sufficient energy so as to exceed a pacing energy stimulation threshold of the chamber, a method for determining the pacing energy stimulation threshold while providing reliable capture of the chamber. The method includes the steps of repeatedly applying electrical pulse pairs to the chamber, each electrical pulse pair including a first pulse and a second pulse, the first pulse preceding the second pulse and being of lesser energy than the second pulse. The first and second pulses evoke a first response and a second response respectively of the heart. The method further includes the steps of comparing the first response to the second response and selecting a minimum necessary pacing energy to effect capture based upon the comparison.

The invention still further provides in a cardiac pacemaker arranged for applying to a chamber of the heart pacing electrical pulses of sufficient energy so as to exceed a pacing energy stimulation threshold of the chamber, a system for determining the pacing energy stimulation threshold including a pulse generator for repeatedly applying pacing electrical pulse pairs to the chamber. Each electrical pulse pair includes a first pulse preceding a second pulse and at least one of the first and second pulses having sufficient energy to exceed the pacing energy threshold of the chamber. The first pulse has an energy less than the energy of the second pulse. The first and second pulses evoke a first response and a second response respectively of the chamber. The system further includes means for comparing the first response to the second response to provide capture values, and threshold selecting means responsive to the capture values changing sign for selecting a pacing energy to effect capture.

BRIEF DESCRIPTION OF THE DRAWINGS

The features of the present invention which are believed to be novel are set forth with particularly in the appended claims. The invention, together with further objects and advantages thereof, may best be understood by making reference to the following description taken in conjunction with the accompanying drawings, in the several figures of which like reference characters identify identical elements, and wherein:

DETAILED DESCRIPTION OF THE INVENTION

Figure 1:
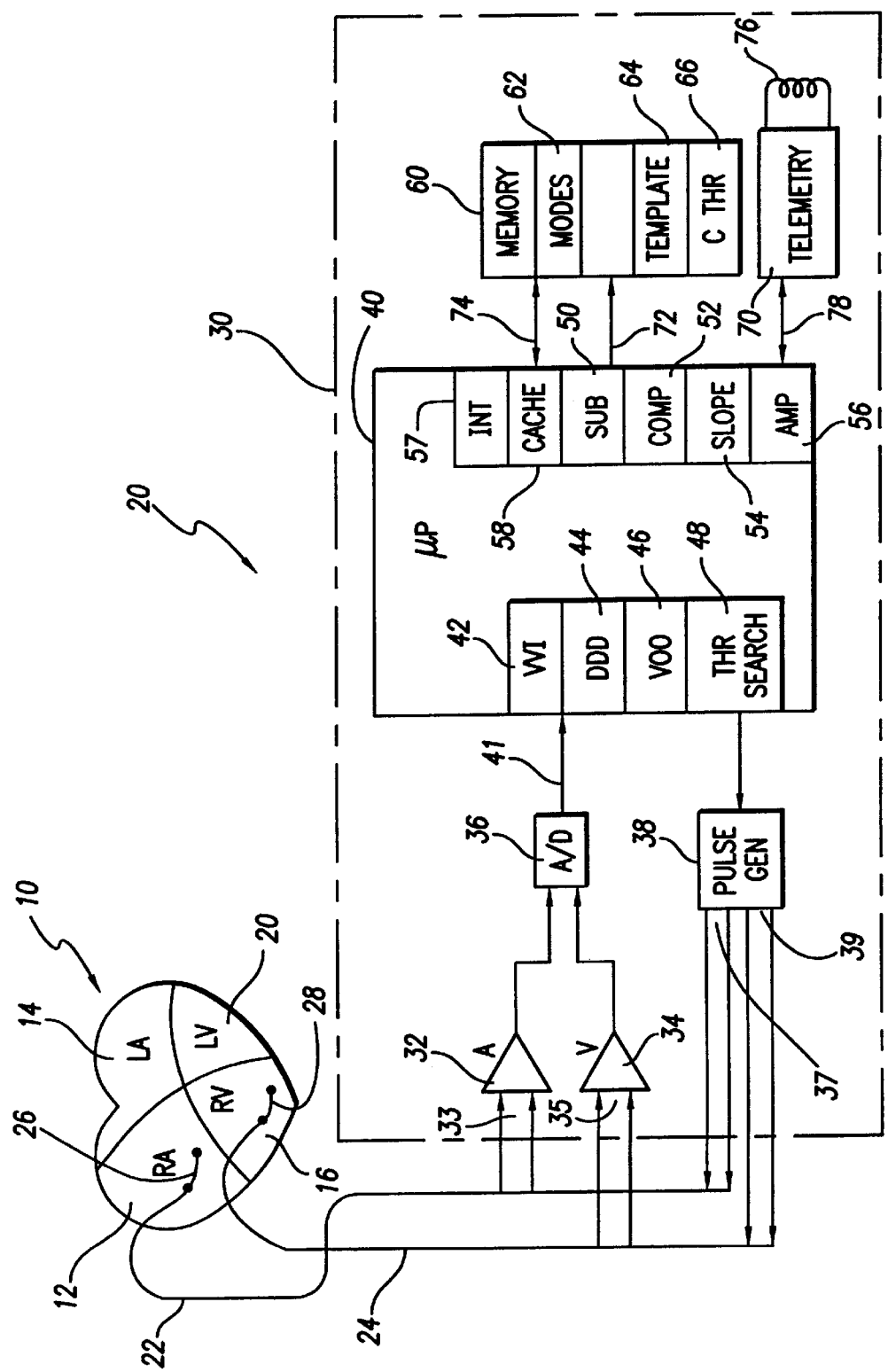
FIG. 1 is a block diagram of a cardiac pacemaker embodying the present invention shown in association with a schematically illustrated heart in need of cardiac rhythm management.

Referring now to FIG. 1, it shows a schematically illustrated heart 10 in need of cardiac rhythm management in association with a cardiac pacemaker 20 embodying the present invention which is coupled to the heart 10 for providing cardiac rhythm management of the heart 10. As illustrated, the heart generally includes a right atrium 12, a left atrium 14, a right ventricle 16, and a left ventricle 20.

The cardiac pacemaker 20 is coupled to the heart 10 by a pair of endocardial leads 22 and 24. Lead 22 is a right atrial lead and includes a bipolar pair of electrodes 26 at its distal end for making electrical contact with the right atrium 12 in a manner well known in the art. Lead 24 is a right ventricle lead and similarly includes a bipolar pair of electrodes 28 at its distal end for making electrical contact with the right ventricle in a manner well known in the art. The cardiac pacemaker 20 includes a hermetic enclosure 30 rendering the cardiac pacemaker 20 fully implantable beneath the skin of a patient. Within the enclosure 30, the cardiac pacemaker 20 includes an atrial sense amplifier 32, a ventricular sense amplifier 34, an analog to digital converter 36, and a pulse generator 38. The cardiac pacemaker 20 further includes a microprocessor 40, a memory 60, and a telemetry stage 70.

The microprocessor 40 is arranged to operate in conjunction with the memory 60 which is coupled to the microprocessor by a multiple-bit address bus 72, and a bi-directional multiple-bit data bus 74. This permits the microprocessor 40 to address desired memory locations within the memory for executing write or read operations. During a write operation, the microprocessor stores data in the memory at the addresses defined on the address bus 72, and conveys the data to the memory 60 over the multiple-bit data bus 74. During a read operation, the microprocessor 40 obtains data or mode defining operating instructions from the memory at the storage locations defined on the address bus 72 and receives the operating instructions and data from the memory over the bi-directional data bus 74. To that end, the memory 60 includes a memory portion 62 which contains operating instructions defining the various operational modes of the cardiac pacemaker 20 such as the VVI mode, DDD mode, or VOO mode. Each of these modes are well known in the art. The memory portion 62 also preferably contains operating instructions defining an automatic threshold search mode embodying the present invention. The memory may also include an additional memory portion 64 for storing data representative of an EGM template and a further memory portion 66 which may store data representing a capture threshold record in accordance with a further aspect of the present invention.

In implementing the program operating instructions contained within memory 60, the microprocessor results in a plurality of functional stages. These stages include a VVI mode stage 42, a DDD mode stage 44, a VOO mode stage 46, and an automatic threshold search stage 48 embodying the present invention. The functional stages also include a subtractor stage 50, a comparison stage 52, a slope-determining stage 54, an amplitude-determining stage 56, and an integrator stage 57. Lastly, the microprocessor 40 includes an internal cache 58 for locally storing data required in the execution, for example, of the automatic threshold search 48 embodying the present invention.

As illustrated in FIG. 1, the lead 22 couples the electrode pair 26 to the inputs 33 of the atrial sense amplifier 32. The atrial sense amplifier 32 thus provides at its output an electrogram representing the atrial activity of the right atrium 12. Although not illustrated, the atrial sense amplifier 32 may be provided with bandpass filtering in a manner well known in the art.

Similarly, the lead 24 couples the electrode pair 28 within the right ventricle to the inputs 35 of the ventricular sense amplifier 34. The ventricular sense amplifier 34 thus provides an electrogram representing the ventricular activity of the right ventricle. The ventricular sense amplifier 34 may also be provided with bandpass filtering as is well known in the art.

The atrial and ventricular electograms are inputted to the analog to digital converter 36. The analog to digital converter 36 is preferably a multiplexing analog to digital converter to provide the microprocessor 40 at an input 41 with digital samples representing both the atrial activity and the ventricular activity of the heart 10.

The lead 22 further couples the electrode pair 26 to the atrial output 37 of pulse generator 38. This permits the pulse generator 38 to provide pacing pulses to the right atrium. Similarly, lead 24 couples the electrode pair 28 to the ventricular output 39 of pulse generator 38. This permits the pulse generator 38 to provide pacing pulses to the right ventricle. Such arrangements are also well known in the art.

Lastly, the telemetry stage 70 permits the cardiac pacemaker 20 to communicate with the outside world, and more particularly, with an external programmer. To that end, the telemetry stage 70 includes a receiving and transmitting coil antenna 76. It is coupled to the microprocessor 40 over a bi-directional bus 78 to permit the microprocessor 40 to output data to the external programmer by way of the telemetry stage 70 or to receive programming parameters from the external programmer. Again, such arrangements are well known in the art.

In accordance with the present invention, automatically, at predetermined times, or under command by the external programmer, the cardiac pacemaker 20 enters the automatic pacing energy stimulation threshold search routine 48 for either the right atrium or the right ventricle. For purposes of this discussion, it will be assumed that the cardiac pacemaker 20 has entered the threshold search routine for the right ventricle 16 of the heart 10.

In carrying out the automatic threshold search, the pulse generator 38 of the cardiac pacemaker 20 repeatedly applies pacing electrical pulse pairs to the right ventricle. Each electrical pulse pair includes a first pulse and a second pulse. The first pulse precedes the second pulse and is than lesser energy of the second pulse. However, the first applied first pulse is of sufficient energy so as to readily assure capture of the right ventricle with the first pulse at the start of the routine.

The first and second pulses of each pulse pair evoke a first response and a second response respectively of the chamber. After each pulse pair is applied to the right ventricle, the first response and the second response are compared to provide capture values. More specifically, the second response is subtracted by the subtractor stage 50 from the first response to provide capture values. Normally, when the first pulse of a pulse pair captures the right ventricle, the capture value will be substantial, relatively constant, and of a distinct polarity. However, when a first pulse amplitude drops below the capture threshold, the capture value subtraction will yield a capture value which is substantial and of the opposite polarity. When this occurs, the capture threshold of the right ventricle will be defined as the last first pulse amplitude that captured the heart.

Even though the last applied first pulse will not capture the heart, because the second pulse of that pulse pair is greater in energy than the first pulse, the right ventricle will still be captured by the second pulse to maintain cardiac rhythm management of the patient.

Figure 2:
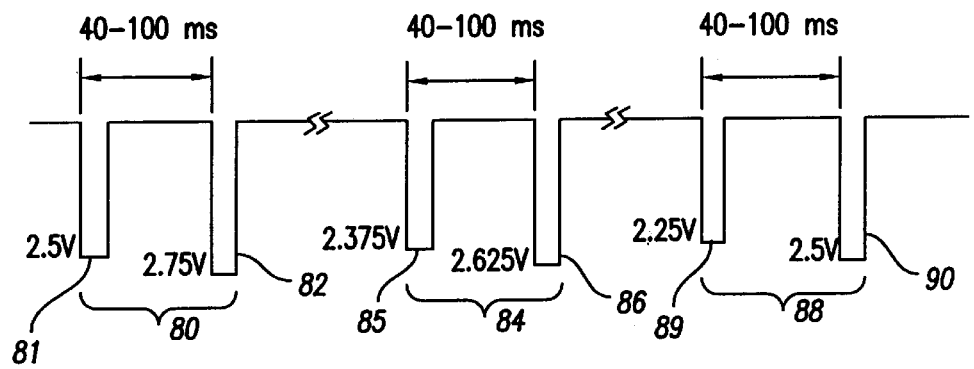
FIG. 2 is waveform showing illustrative pacing pulse pairs repeatedly applied to a heart chamber in accordance with the present invention.

The foregoing is more particularly illustrated in FIG. 2 to which reference is now made. As will be seen in FIG. 2, the pulse generator 38 repeatedly provides pacing electrical pulse pairs 80, 84, and 88 preferably at a rate above the sinus rate of the heart 10, as for example, 70–90 pulse pairs per minute. Pulse pair 80 includes a first pulse 81 and a second pulse 82. Pulse pair 84 includes a first pulse 85 and a second pulse 86. Finally, pulse pair 88 includes a first pulse 89 and a second pulse 90. As will be noted in FIG. 2, each of the first pulses 81, 85, and 89 precedes its corresponding second pulse 82, 86, and 90 respectively. Also, each of the first pulses 81, 85 and 89 is of lesser energy than its corresponding second pulse 82, 86, and 90. More specifically, the pulse generator 38 will have a programmable pulse amplitude increment resolution. For example, the pulse amplitude increment resolution of the pulse generator 38 may be 0.125 volts.

In accordance with this preferred embodiment, the energy of each of the first pulses is selected so as to be at least one and preferably two resolution increments less than its corresponding second pulse. To that end, as may be further noted in FIG. 2, each of the first pulses is 0.250 volts less than its corresponding second pulse.

Each of the first and second pulses is of the same pulse width. As may be appreciated by those skilled in the art, the energies of the first and second pulses may be rendered different in accordance with this preferred embodiment by varying the pulse width of the pulses instead of the voltage amplitudes. Further, the various energies may be obtained by varying the applied currents while maintaining the pulse widths constant. As a result, all such manners of varying the energy of the pulses are considered to fall within the true spirit and scope of the present invention.

Referring again to FIG. 2, each first and second pulse pair is separated in time by a rather small time interval of, for example, 40–100 milliseconds. The energy of the first pulse 81 is selected to assure that it is above the capture threshold of the right ventricle for beginning the automatic threshold search.

As will also be noted in FIG. 2, the energy of the first and second pulses of successive pulse pairs are decremented. In accordance with this preferred embodiment, the successive first and second pulse pairs are decremented by an equal amount of, for example, the energy resolution increment of the pulse generator 38 or 0.125 volts.

Figure 3:
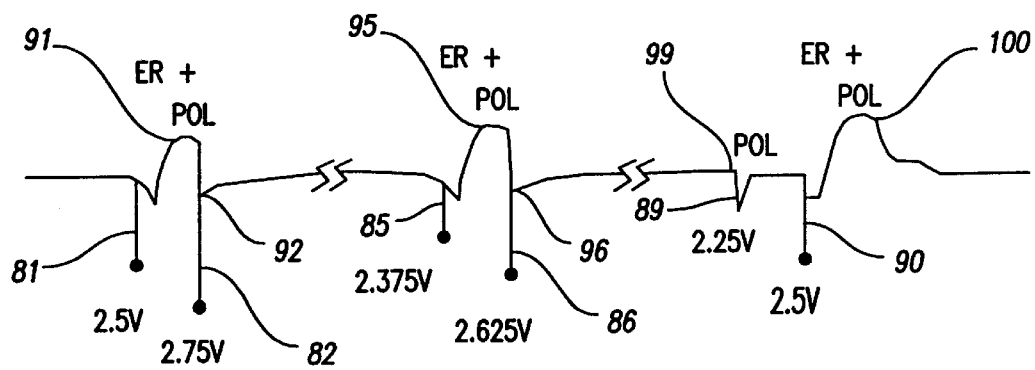
FIG. 3 is an EGM waveform of an illustrative response of a heart to the pacing pulse pairs illustrated in FIG. 2.

As will be seen in FIG. 3, the first and second pulses of each pulse pair evoke a first and second response respectively of the right ventricle. The first pulse 81 captures the right ventricle to provide a peak response 91 equal to the evoked response plus polarization (ER+POL). The second pulse 82, by being closely spaced to the first pulse 81, only evokes the polarization response (POL) 92.

Following the pulse pair 81 and 82, the second response 92 is subtracted from the first response 91. As can be appreciated from FIG. 3, this will result in a capture value which is substantial and of positive polarity.

The next pulse pair applied to the right ventricle including the first pulse 85 and second pulse 86 evoke the first response 95 and second response 96. Here it can also be seen that the first pulse 85 of this pulse pair has captured the right ventricle. Hence, when the second response 96 is subtracted from the first response 95, the capture value thus obtained will once again be substantial and of positive polarity. It will also be substantially equal to the capture value obtained from responses 91 and 92.

The pulse pair 88 renders a different result. Here it can be seen that the first pulse 89 of this pair has failed to capture the right ventricle and yields only the polarization (POL) response 99 while the second pulse 90 of this pulse pair captures the right ventricle to yield the ER+POL response 100. Now, when the second response 100 evoked by the pulse 90 is subtracted from the response 99 evoked by pulse 89, the resulting capture value will also be substantial but of opposite polarity compared to the capture values previously obtained. At this point, the autothreshold search routine may be completed by setting the pacing pulse amplitude at the last capturing first pulse amplitude plus the incremental resolution of the pulse generator. In accordance with this embodiment, that value would be the voltage of pulse 85 or 2.375 volts plus the incremental resolution of the pulse amplifier or 0.125 volts yielding a pacing pulse amplitude of 2.50 volts.

At no time during the automatic pacing energy stimulation threshold search was capture of the right ventricle lost. This is due to the fact that at least one of the first and second pulses of each pulse pair has an energy greater than the energy required for capturing the right ventricle.

The threshold value thus obtained may be stored by the microprocessor in memory portion 66 to enable the cardiac pacemaker to keep a capture threshold record. Then, the starting point of the next capture threshold test need not be the maximum programmable pulse energy, but rather a value between the maximum programmable pulse energy and the last recorded capture threshold (e.g., the average of the two).

For purposes of isolating the capture response from the polarization response of each pacing pulse pair, the comparison stage 52 may be utilized to conduct a morphology comparison by a point-by-point waveform comparison of responses stored in cache 58 with a template previously stored in memory portion 64 of memory 60. The capture response may be further, or alternatively, discriminated from the polarization response by feature extraction such as slope-determination using slope stage 54, peak or average amplitude using amplitude-determining stage 56 or an integral of the response using integrator stage 57. All such techniques are well known in the art. In addition to the foregoing, the discrimination of the polarization response from the capture response can be made using the polarization response from the backup pulse of the present pulse pair or from the prior pulse pair. A more accurate discrimination may be made if the polarization response from the present pulse pair is used, however, since the most recent polarization response will be generated from a pacing pulse closer in amplitude to its corresponding primary pulse.

Figure 4:
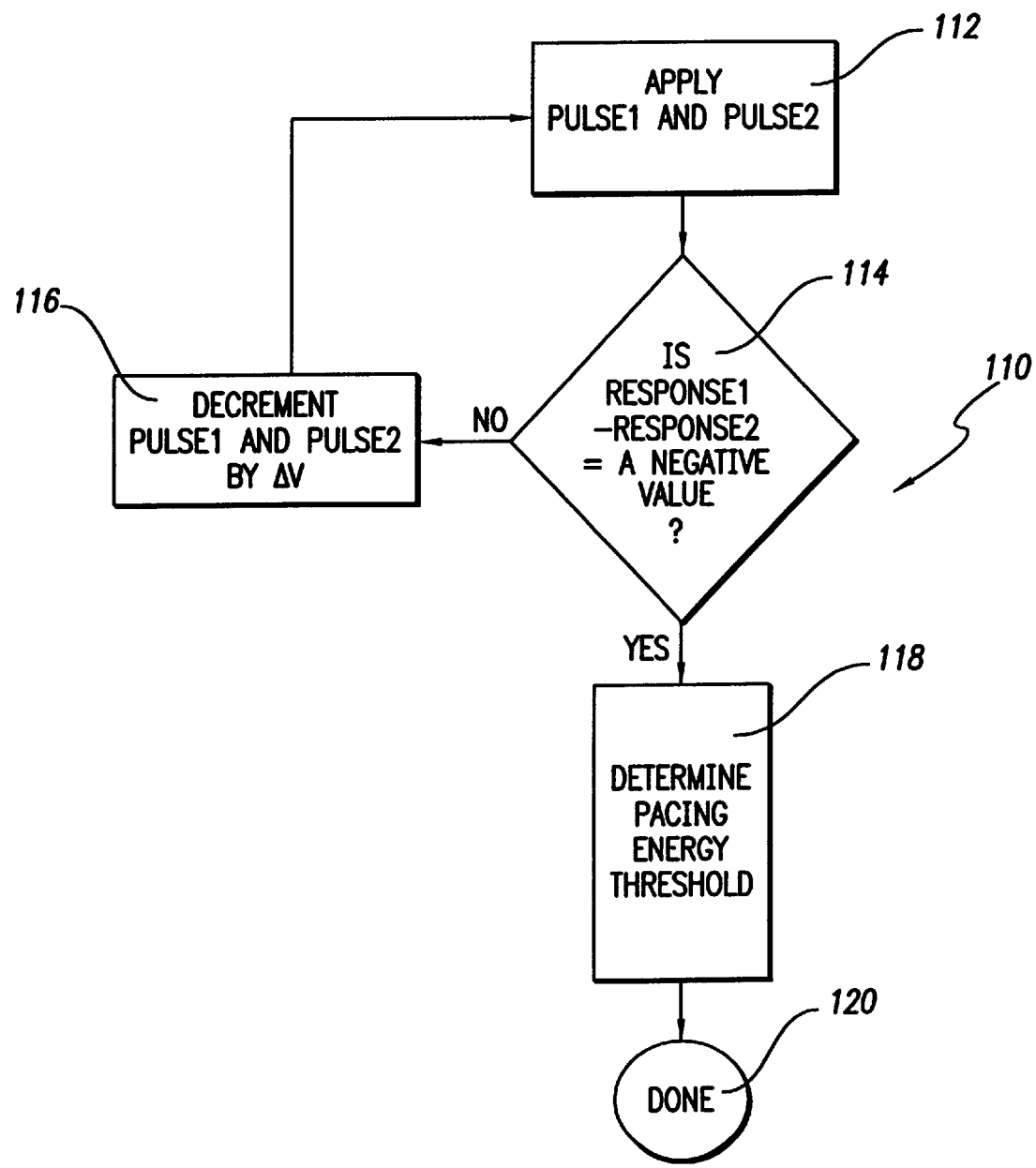
FIG. 4 is a flow diagram of the basic steps employed in an autothreshold determination embodying the present invention.

Referring now to FIG. 4, it illustrates a flow diagram 110 which essentially summarizes the methodology described with respect to FIGS. 2 and 3. When the cardiac pacemaker 20 enters the automatic threshold search routine, it first applies a first pulse and a second pulse in accordance with step 112. As previously mentioned, the energy of the first pulse is less than the energy of the second pulse and precedes the second pulse. The first pulse and the second pulse will evoke first and second responses respectively of the heart chamber. In accordance with step 114, the second response is subtracted from the first response to yield a capture value. In accordance with step 114, it is queried whether the capture value is negative. If the capture value is not negative, that will mean the first pulse captured the chamber and the second pulse evoked the polarization response. As a result, the energies of the first and second pulses are decremented in accordance with step 116 and the process returns to step 112.

When the capture value is negative as determined in step 114, the process then continues to step 118 wherein the pacing energy stimulation threshold of the chamber is determined. As previously mentioned, the energy threshold may be determined as being the first pulse energy last capturing the chamber plus the incremental energy resolution of the pulse generator. Once the capture threshold is determined in accordance with step 118, the process is completed.

Once the foregoing process is completed, the energy to be delivered to the chamber may be selected so as to be above the determined capture threshold pacing energy. For example, in accordance with this embodiment, the energy to be applied to the chamber may be, for example, 0.5 volts above the determined threshold. This will assure reliable capture of the chamber whenever a pacing pulse is applied to the chamber.

While a particular embodiment of the present invention has been shown and described, modifications may be made. For example, while endocardial leads have been shown and described herein, those skilled in the art will readily realize that the invention pertains equally as well to and may be practiced with epicardial leads and intravascular leads. Also, the invention may be practiced in unipolar pacing wherein the device enclosure is electrically conductive and used as a common electrode in a manner well known in the art. Hence, it is therefore intended in the appended claims to cover all such changes and modifications which fall within the true spirit and scope of the invention.

What is claimed is:

1. In a cardiac pacemaker arranged for applying to a chamber of a heart pacing electrical pulses of sufficient energy so as to exceed a pacing energy stimulation threshold of the chamber, a system for determining the pacing energy stimulation threshold comprising:
   a pulse generator for repeatedly applying pacing electrical pulse pairs to the chamber, each electrical pulse pair including a first pulse and a second pulse, the first pulse preceding the second pulse and being of lesser energy than the second pulse according to a predetermined relationship, the first and second pulses for evoking a first response and a second response respectively of the chamber;
   means for comparing the first response to the second response to provide capture values; and
   threshold selecting means responsive to the capture values for selecting a pacing energy stimulation threshold.

2. The system, as defined in claim 1, further including means for decrementing the energy of the first and second pulses of successive pulse pairs until the threshold selecting means selects a pacing energy stimulation threshold.

3. The system, as defined in claim 1, wherein the means for comparing include a subtractor for subtracting the magnitude of the second response from the magnitude of the first response.

4. The system, as defined in claim 1, wherein the pulse generator has an energy resolution increment and wherein the energy of the first pulse is at least one energy resolution increment less than the energy of the second pulse.

5. The system, as defined in claim 1, wherein the pulse generator has an energy resolution increment and wherein the system further includes means for decrementing the energy of the first and second pulses of successive pulse pairs by at least one energy resolution increment until the threshold select means selects a pacing energy threshold.

6. The system, as defined in claim 1, wherein the comparing means provides capture values corresponding to the difference between the first and second responses and the threshold selecting means is responsive to a transition between a positive and a negative capture value for selecting a pacing energy stimulation threshold.

7. The system, as defined in claim 7, wherein the threshold selecting means bases the pacing energy stimulation threshold upon the energy of the first pulse of the pulse pair applied immediately prior to the pulse pair causing a transition between a positive and a negative capture value.

8. The system of claim 1 wherein each pulse is characterized by an amplitude and the amplitude of the second pulse is selected to exceed the amplitude of the first pulse by a predetermined amount.

9. A method for determining the pacing energy stimulating threshold for a chamber of a heart, the method comprising the steps of:
   repeatedly applying pacing electrical pulse pairs to the chamber, each electrical pulse pair including a first pulse and a second pulse, the first pulse preceding the second pulse and being of lesser energy than the second pulse according to a predetermined relationship, the first and second pulses for evoking a first response and a second response respectively of the chamber;

comparing the first response to the second response; and
selecting a pacing energy stimulation threshold based upon the comparison.

10. The method, as defined in claim 9, further including the step of decrementing the energy of the first and second pulses of successive pulse pairs until a pacing energy stimulation threshold is selected based upon the comparing step.

11. The method, as defined in claim 9, wherein the comparing step includes subtracting the magnitude of the second response from the magnitude of the first response.

12. The method, as defined in claim 9, wherein the pulse generator has an energy resolution increment and wherein the repeatedly applying step involves setting the energy of the first pulse to be at least one energy resolution increment less than the energy of the second pulse.

13. The method, as defined in claim 9, wherein the pulse generator has an energy resolution increment and wherein the method further includes the step of decrementing the energy of the first and second pulses of successive pulse pairs by at least one energy resolution increment until the threshold select means selects a pacing energy stimulation threshold according to the comparing step.

14. The method, as defined in claim 9, wherein the comparing step includes generating capture values corresponding to the difference between the first and second responses and wherein the selecting step is performed when there is a transition between a positive and a negative capture value.

15. The method, as defined in claim 14, wherein the selecting step includes the step of basing the pacing energy stimulating threshold upon the energy of the first pulse of the pulse pair applied immediately prior to the pulse pair causing a transition between a positive and a negative capture value.

16. The method of claim 9 wherein each pulse is characterized by an amplitude, the method additionally comprising the step of setting the amplitude of the second pulse to a level that exceeds the amplitude of the first pulse by a predetermined amount.

17. In a cardiac pacemaker arranged for applying to a chamber of a heart pacing electrical pulses of sufficient energy so as to exceed a pacing energy stimulation threshold of the chamber, a system for determining the pacing energy stimulation threshold comprising:

a pulse generator for repeatedly applying pacing electrical pulse pairs to the chamber, each electrical pulse pair including a first pulse preceding a second pulse and at least one of the first and second pulses having sufficient energy to exceed a pacing energy stimulation threshold of the chamber, the first pulse being of lesser energy than the second pulse according to a predetermined relationship, the first and second pulses for evoking a first response and a second response respectively of the chamber;

means for comparing the first response to the second responses to provide capture values corresponding to the difference between the first and second responses; and threshold select means responsive to a transition between a positive and a negative capture value for selecting a pacing energy stimulation threshold.

18. The system of claim 17 wherein each pulse is characterized by an amplitude and the amplitude of the second pulse is selected to exceed the amplitude of the first pulse by a predetermined amount.

19. A cardiac stimulation device configured for determining the pacing stimulation threshold for stimulating cardiac tissue in a chamber of a heart, the stimulation device comprising:

a pulse generator configured to generate a pair of stimulation pulses at controlled amplitudes, wherein each pair of stimulation pulses includes a first pulse and second pulse, the first pulse preceding the second pulse and having an amplitude less than the second pulse according to a predetermined relationship;

a detection circuit configured to receive first and second responses from the cardiac tissue in response to the first and second pulses;

a subtractor circuit configured to determine the difference in the amplitudes of the first and second responses;

a controller which determines that the first pulse is below the pacing stimulation threshold when the difference between the first and second responses transitions from a positive to a negative value; and wherein the controller periodically decrements the amplitude of each of the pulses of the pair of stimulation pulses until the controller determines that the amplitude of the first pulse is below the pacing stimulation threshold; whereby the controller determines the pacing stimulation threshold.

20. The cardiac stimulation device of claim 19 wherein the amplitude of the second pulse is selected to exceed the amplitude of the first pulse by a predetermined amount.

21. The cardiac stimulation device of claim 19 wherein the first and second pulses of each pair of stimulation pulses are separated by a predetermined time period between 40 and 100 milliseconds.

22. The cardiac stimulation device of claim 19 wherein the determined pacing stimulation threshold correspond to the amplitude of the first pulse of the pair of stimulation pulses applied prior to detecting a positive to negative transition of the difference between the first and second responses.

* * * * *